Jan. 31, 1956 M. TANTAU Plant Pat. 1,454
ROSE PLANT
Filed March 11, 1955
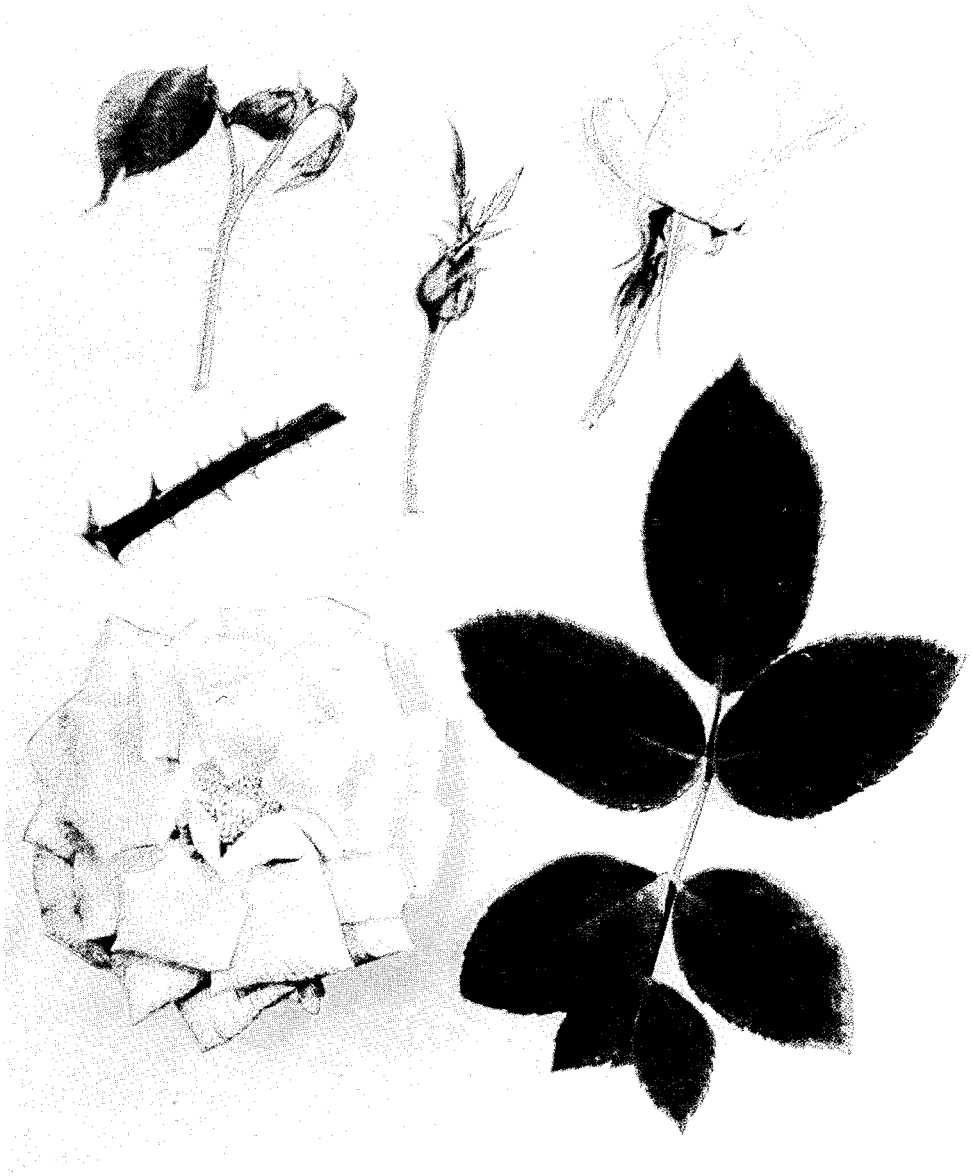
Inventor
Mathias Tantau
By: Robb & Robb
Attorneys.

United States Patent Office

Plant Pat. 1,454
Patented Jan. 31, 1956

1,454

ROSE PLANT

Mathias Tantau, Uetersen, Holstein, Germany, assignor to Jackson & Perkins Company, Newark, N. Y., a corporation of New York Application March 11, 1955, Serial No. 493,845

1 Claim. (Cl. 47—61)

The present invention relates to a new and distinct variety of rose plant of the hybrid tea class, which was originated by me by crossing the variety "Danzig" (unpatented) with an unnamed and unpatented seedling derived from a cross of "Crimson Glory" (Plant Patent No. 105) and another unnamed and unpatented sister seedling of "Floradora" (unpatented).

The primary object of this breeding was to produce a new variety of rose plant which bears flowers of larger size and of a new color in the multibracteata strain. This objective was fully attained in my new variety, along with other improved and desirable characteristics which contribute to the novelty and distinctiveness thereof. In this connection, my new variety is particularly characterized by the following outstanding features:

(1) The hooked leaves and the prominent bracts of the plant;

(2) The variation from 1 to 7 leaflets and the prominent hooks on each leaflet;

(3) The prominent thorns, prickles and needles;

(4) The good size of the blooms which are borne on stems which have the characteristics of the original specie multibracta that was one of the parents of the pollen parent;

(5) The unusual stiffness of the flower petals;

(6) The fruity fragrance of the blooms; and (7) The distinctive scarlet general color tonality of the blooms.

The foregoing characteristics and distinctions of my new variety definitely differentiate the same from its parents, as well as from all other varieties of this class of which I am aware, and asexual reproduction of my new variety by budding, as performed at Newark, New York, U. S. A., and also at Pleasanton, California, U. S. A., shows that these characteristics and distinctions come true to form and are established and transmitted through succeeding propagations.

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature;

Parentage—Seedling:
- *Seed parent.*—"Danzig."
- *Pollen parent.*—An unnamed seedling of "Crimson Glory" X an unnamed sister seedling of "Floradora."

Classification:
- *Botanic.*—Hybrid tea.
- *Commercial.*—Hybrid tea.

FLOWER (Observations made from specimens grown in a greenhouse at Newark, New York, U. S. A., in the early morning in the early part of the month of August.)

Blooming habit: Recurrent—continuous.

Bud:
- *Size.*—Medium.
- *Form.*—Ovoid; is not affected by wet or hot weather.
- *Color.*—When sepals first divide—Carmine, Plate 1. When petals begin to unfurl—Carmine, Plate 1, lightly overcast with Spectrum Red, Plate 1. When half blown: inside of petals—Scarlet, Plate 1, lightly overcast with Grenadine Red, Plate 2; reverse of petals—Spectrum Red, Plate 1, lightly overcast with Rose Doree, Plate 1.
- *Sepals.*—Branched, with "hood" above bud; curl back when petals begin to unfurl. Color: inside—Kildare Green, Plate 31; outside—Light Cress Green, Plate 31.
- *Calyx.*—Shape—funnel. Size—small. Aspect—smooth. Odor when rubbed—none. Color—Parrot Green, Plate 6.
- *Peduncle.* — Length — medium. Aspect — rough. Strength—erect; slender. Color—Biscay Green, Plate 17.
- *Opening.*—Opens up well; is not affected by adverse weather conditions.

Bloom:
- *Size.*—Medium. Average size when fully expanded—from 3½ inches to 4½ inches.
- *Borne.*—Singly and several together.
- *Stems.*—Medium length; normal strength.
- *Form (when first open).*—High center. Permanence—flattens; outer petals curl back.
- *Petalage.*—Double (full but open center). Number of petals under normal conditions—from 15 to 20.
- *Color.*—Center of flower—Scarlet Red, Plate 1. Outer petals—Scarlet, Plate 1, lightly overcast with Peach Red, Plate 1. Base of petals (aiglet)—Strontian Yellow, Plate 16. Inside of petals—Scarlet, Plate 1, lightly overcast with Grenadine Red, Plate 2. Reverse of petals—Rose Red, Plate 12, lightly overcast with Begonia Rose, Plate 1. General tonality from a distance—Scarlet, Plate 1.
- *Discoloration.*—General tonality at end of first day—Scarlet Red, Plate 1. Second day—Scarlet, Plate 1. Third day—Scarlet Red, Plate 1, lightly overcast with Grenadine Red, Plate 2.

Petals:
- *Texture.*—Leathery; very stiff; is not affected by wet or hot weather.
- *Appearance.*—Inside—satiny; outside—shiny.
- *Form.*—Oval; scalloped.
- *Arrangement.*—Irregular.
- *Petaloids in center.*—Few; large.
- *Persistence.*—Drop off cleanly.
- *Fragrance.*—Moderate. Nature—fruity (russet apple).
- *Lasting quality.*—On the plant—long. As cut flower—long.

GENITAL ORGANS

Stamens, anthers: Medium size; many.
- *Arrangement.*—Regular around styles.
- *Color.*—Tawny, Plate 15.

Stamens, filaments (threads): Medium length.
- *Color.*—Spinel Red, Plate 26.

Pollen:
- *Color.*—Light Ochraceous Salmon, Plate 15.

Styles: Loosely separated; uneven length; short; thin.

Stigmas:
- *Color.*—Warm Buff, Plate 15.

Ovaries: Some protruding from calyx.

Hips: None.

Seeds: None.

PLANT

Form: Bush.

Growth: Vigorous; upright; corresponds to characteristic multibracteata growth.

Foliage: From 1 to 7 leaflets.

*Size.*—Medium.

*Quantity.*—Abundant.

*Color.*—New foliage: upper side—Parrot Green, Plate 6, lightly overcast with Victoria Lake, Plate 1; under side—Yellowish Oil Green, Plate 5, lightly overcast with Carmine, Plate 1. Old foliage: upper side—Forest Green, Plate 17; under side—Light Cress Green, Plate 31.

*Shape.*—Oval pointed.

*Texture.*—Upper side—leathery; under side—smooth.

*Ribs and veins.*—Light.

*Edge.*—Serrated (saw-toothed).

*Serration.*—Both double and single; small.

*Leaf stem.* — Color — Absinthe Green, Plate 31. Under side—with prominent hooks.

*Stipules.*—Long; bearded.

Wood:

*New wood.* — Color—Biscay Green, Plate 17. Bark—smooth.

*Old wood.*—Color—Bice Green, Plate 17. Bark—smooth.

Thorns:

*Thorns.*—Quantity: on main stalks from base—many; on laterals from stalk—many. Form—medium length; some straight and some hooked downward. Color (when young)—Venetian Pink, Plate 13. Position—irregular.

*Prickles.*—Quantity: on main stalks—many; on laterals—many. Color—Hermosa Pink, Plate 1.

*Short needles.*—Quantity: on main stalks—many; on laterals—many.

I claim:

A new and distinct variety of rose plant of the hybrid tea class, substantially as herein shown and described, characterized particularly as to novelty by its hooked leaves and prominent bracts, its compound leaves composed of from 1 to 7 leaflets, with prominent hooks on each leaflet, the prominent thorns, prickles and needles, the good size of the blooms which are borne on stems having characteristics of its antecedent specie multibracta, the unusual stiffness of the flower petals, the fruity fragrance of the blooms, and the distinctive Scarlet Red general color tonality of the blooms.

No references cited.